United States Patent
Ferrando et al.

(10) Patent No.: US 10,590,053 B2
(45) Date of Patent: Mar. 17, 2020

(54) PROCESS TO PRODUCE A BIO-PRODUCT

(71) Applicant: VALMET AKTIEBOLAG, Sundsvall (SE)

(72) Inventors: Patrizia Ferrando, Lu (IT); Marco Bernardi, Bologna (IT); Dario Giordano, Tortona (IT); Lari Lammi, Pori (FI); Mats Nordgren, Bromma (SE)

(73) Assignee: VALMET AKTIEBOLAG, Sundsvall (SE)

( * ) Notice: Subject to any disclaimer, the term of this patent is extended or adjusted under 35 U.S.C. 154(b) by 0 days.

(21) Appl. No.: 15/780,718

(22) PCT Filed: Dec. 1, 2016

(86) PCT No.: PCT/SE2016/051195
§ 371 (c)(1),
(2) Date: Jun. 1, 2018

(87) PCT Pub. No.: WO2017/095313
PCT Pub. Date: Jun. 8, 2017

(65) Prior Publication Data
US 2018/0362423 A1 Dec. 20, 2018

(30) Foreign Application Priority Data
Dec. 3, 2015 (EP) .................................... 15425105

(51) Int. Cl.
*C07C 29/09* (2006.01)
*D21C 5/00* (2006.01)
*D21C 11/00* (2006.01)
*C07C 51/00* (2006.01)

(52) U.S. Cl.
CPC .............. *C07C 29/09* (2013.01); *C07C 51/00* (2013.01); *D21C 5/00* (2013.01); *D21C 11/0007* (2013.01)

(58) Field of Classification Search
CPC ..... C07C 29/09; C07C 51/00; D21C 11/0007; D21C 5/00
See application file for complete search history.

(56) References Cited

U.S. PATENT DOCUMENTS

| 5,125,977 A | 6/1992 | Grohmann et al. |
| 5,705,369 A | 1/1998 | Torget et al. |
| 6,022,419 A * | 2/2000 | Torget .................... C07G 17/00 127/1 |
| 8,262,854 B2 | 9/2012 | Uusitalo et al. |
| 2010/0313882 A1 | 12/2010 | Dottori et al. |
| 2011/0192560 A1* | 8/2011 | Heikkila ............... C13B 20/148 162/29 |
| 2011/0312051 A1 | 12/2011 | Kalnes et al. |
| 2014/0356915 A1 | 12/2014 | Retsina et al. |

FOREIGN PATENT DOCUMENTS

| EP | 2 430 233 B1 | 5/2013 |
| WO | WO 2010/114468 A1 | 10/2010 |
| WO | WO 2015/028156 A1 | 3/2015 |

OTHER PUBLICATIONS

Mao H. et al., "Technical Economic Evaluation of a Hardwood Biorefinery Using the "Near-Neutral" Hemicellulose Pre-Extraction Process", Journal of Biobased Materials and Bioenergy, vol. 2, No. 2, 2008, pp. 177-185.

* cited by examiner

*Primary Examiner* — Yevgeny Valenrod
*Assistant Examiner* — Blaine G Doletski
(74) *Attorney, Agent, or Firm* — Foley & Lardner LLP

(57) ABSTRACT

It is disclosed a process to produce a bio-product starting from a ligno-cellulosic feedstock, comprising a pre-hydrolysis step of the ligno-cellulosic feedstock in one or more pre-hydrolysis vessels to produce a liquid pre-hydrolyzate comprising water and water soluble hemicellulose, followed by a multi-step hydrolysis of the water soluble hemicellulose. The hydrolysis steps are conducted in separated vessel. The liquid pre-hydrolyzate is subjected to a partial hydrolysis step in a first hydrolysis vessel, to produce a first hydrolyzate. A portion of the first hydrolyzate, comprising remnant water soluble hemicellulose, is recirculated in at least one pre-hydrolysis vessel and subjected to a second hydrolysis step. Another portion of the first hydrolyzate comprising monomeric sugars is removed and converted to the bio-product, preferably after a refining hydrolysis step. The process also produces a hemicellulose-depleted feedstock which is preferably treated to produce a cellulosic pulp. The bio-product comprises any chemical from the groups of polyols, diols, alcohols, and carboxylic acids, or lactic acid or the group consisting of ethylene glycol, propylene glycol, or a mixture thereof.

27 Claims, 4 Drawing Sheets

PROCESS TO PRODUCE A BIO-PRODUCT

BACKGROUND

In the pulp industry, different processes are used for producing a cellulosic pulp from ligno-cellulosic feedstocks, typically softwoods and hardwoods. Even if also mechanical treatments may be used, most diffused processes comprise a cooking treatment of the ligno-cellulosic feedstock with chemicals for solubilizing the majority of the lignin and the hemicellulose, thereby producing a cellulosic fiber suspension in liquid solution called "brown stock". By means of washing treatments, the brown stock is separated in a stream comprising the cellulosic fibers and one or more effluent streams, comprising the spent cooking chemicals and the solubilized lignin and hemicellulose. The clean pulp (stock) can be bleached in the bleach plant or left unbleached, depending on the end use.

In the dissolving pulp process, which is used to produce high purity cellulose end-product, at least a portion of the hemicellulose of the ligno-cellulosic feedstock is solubilized by means of a hydro-thermal pre-hydrolysis process prior to treating the ligno-cellulosic feedstock depleted of the extracted hemicellulose with chemicals.

Examples of pre-hydrolysis processes may be found in U.S. Pat. No. 8,262,854 and EP2430233.

In U.S. Pat. No. 8,262,854 it is disclosed an improved method for treating lignocellulosic material, including a prehydrolysis-mass transfer process, which produces a concentrated hydrolysate volume during the time required for the hydrolysis itself. The improved process comprises the heating of the digester and chip content by direct steam to the required hydrolysis temperature, starting a flow of hot, stored hydrolysate to the top of the chip bed in order to create a trickle-bed type down-flow of hydrolysate, collecting a first fraction of the trickled-down hydrolysate as a product fraction, adding extraction liquid and continuing the trickle flow to collect a second hydrolysate fraction, which will be discharged from the digester to a hot hydrolysate storage tank to be used as the first trickle flow liquid in the next batch.

In EP2430233 it is disclosed a displacement batch cooking process comprising a steam-phase prehydrolysis step, wherein the recovery of the by-products is improved. In the recovery step of the present invention, after the target P-factor in the prehydrolysis stage is reached, hot washing liquid is introduced into the digester from the bottom thereof. The washing liquid is circulated via the suction screens to the top and to the bottom of the digester until the prehydrolyzed chips are under the washing liquid. The hot washing liquid containing by-products is recovered from the digester and the digester contents are neutralized by displacing the washing liquid with alkaline liquor.

A common feature to all the processes in the pulp industry is the fact that they are very energy intensive. The effluent streams are usually sent to a recovery boiler, wherein they are burned generating heat from the solubilized lignin and hemicellulose. In the recovery boiler, chemicals are also recovered from the effluent stream and recycled in the process. As heat is a low value product, the conventional pulping processes only take a partial advantage from the ligno-cellulosic feedstock. Considering that hemicellulose has a low heating value, about half of that of lignin, burning hemicellulose to produce heat is not a convenient strategy for hemicellulose valorization. Moreover, the effluent streams, coming from the washing steps, are diluted and they must be subjected to many evaporation steps to increase the dry matter content before being burned, at the expenses of the energy balance.

The conversion of monomeric sugars to bio-chemicals or a bio-product is also known in the art. In this application is bio-chemicals or bio product referred to as any chemical from the groups of polyols, diols, alcohols, and carboxylic acids, or lactic acid or the group consisting of ethylene glycol, propylene glycol, or a mixture thereof. I.e. conversion products obtainable from monomeric sugars. U.S. Pat. No. 8,198,486 discloses methods for generating propylene glycol, ethylene glycol and other polyols, diols, ketones, aldehydes, carboxylic acids and alcohols from biomass. The methods involve reacting a portion of an aqueous stream of a biomass feedstock solution over a catalyst under aqueous phase reforming conditions to produce hydrogen, and then reacting the hydrogen and the aqueous feedstock solution over a catalyst to produce a generic mixture of propylene glycol, ethylene glycol and the other polyols, diols, ketones, aldehydes, carboxylic acids and alcohols.

US20110312051 disclosed a process for generating at least one polyol from a feedstock comprising saccharide performed in a continuous or batch manner. The process involves contacting hydrogen, water, and a feedstock comprising saccharide, with a catalyst system to generate an effluent stream comprising at least one polyol and recovering the polyol from the effluent stream. The polyol may be selected from the group consisting of ethylene glycol and propylene glycol.

In the biorefinery concept, different integrated processes for converting hemicellulose to various value-added products, such as polyols, alcohols, carboxylic acids and many others have been proposed.

As an example, in the process described in Mao H. et al., "Technical economic evaluation of a hardwood biorefinery using the "near-neutral" hemicellulose pre-extraction process", J. Biobased Mater. Bioenergy 2(2) p. 177-185 (2008), a portion of the hemicellulose is extracted from wood prior to pulping and converted into acetic acid and ethanol while using the extracted wood chips to produce Kraft pulp. In the paper, an existing Kraft pulp mill was considered as the base case. The pulp production was maintained constant and the hemicellulose extraction process was added to the fiber line. The hemicellulose extraction process occurs in a separated impregnation vessel prior to the continuous digester for pulp production. The extraction is carried out using green liquor (mostly $Na_2CO_3+Na_2S$). The process disclosed for hemicellulose extraction and conversion to ethanol and acetic acid includes wood extraction for hemicellulose removal, flashing of the extract to produce preheating steam, recycling a portion of the extract back to the extraction vessel for the purpose of raising the solids content of the extract, acid hydrolysis using sulfuric acid for conversion of the oligomeric carbohydrates into monomeric sugars and cleavage of lignin-carbohydrate covalent bonds, filtration to remove precipitated lignin, liquid-liquid extraction followed by distillation to remove acetic acid and furfural from the sugar solution, liming to raise the pH to that required for fermentation, fermentation of five and six-carbon sugars and glucuronic acid to ethanol and finally distillation and upgrading the product to pure ethanol.

There are many issues to be addressed or improved in the integration of pulping processes and hemicellulose conversion processes to value-added products, in order to render the integration effective from a technical or economical point of view.

One issue is related to the increase of hemicellulose extraction in pre-hydrolysis step with a minimal use of added chemicals, such as mineral acids, which are expensive and must be eliminated or recycled in downstream process steps.

As the pre-hydrolysis step produces water soluble hemicellulose mainly in the form of water soluble oligomeric and polymeric sugars, there is the need to hydrolyze the water soluble hemicellulose to monomers, which are then converted to the final product. It is known in the art that the hydrolysis of water soluble hemicellulose to monomers requires more severe process conditions than the pre-hydrolysis step, which may be reached by increasing hydrolysis temperature and/or time, and/or lowering the pH during hydrolysis, with respect to the pre-hydrolysis step. By increasing the hydrolysis time, the volume of the hydrolysis reactor may increase correspondingly to a not manageable size. By increasing the hydrolysis temperature, sugar degradation becomes relevant. As already stated, the use of added mineral acid to lower the pH should be minimized. Thereby, a second issue to be addressed is related to the integration of pre-hydrolysis and hydrolysis step, to obtain a whole process working in balanced process conditions.

A third issue is the production of pre-hydrolysis and hydrolysis streams having a high concentration of water soluble sugars, in polymeric and monomeric form.

All these open issues are solved by the disclosed invention.

BRIEF DESCRIPTION OF THE INVENTION

It is disclosed a process for producing a bio-product from a water insoluble ligno-cellulosic feedstock comprising cellulose, hemicellulose and lignin. The process comprising the steps of: pre-hydrolyzing a portion of the water insoluble hemicellulose in one or more pre-hydrolysis vessels, to produce a liquid pre-hydrolyzate comprising water and water soluble hemicellulose; receiving the liquid pre-hydrolyzate in a first hydrolysis vessel from at least one pre-hydrolysis vessel; subjecting a portion of the liquid pre-hydrolyzate to a first hydrolysis step to produce a first hydrolyzate comprising water, water soluble monomeric sugars and remnant water soluble hemicellulose; adding a recirculated portion of the first hydrolyzate to at least one pre-hydrolysis vessel, removing a hydrolyzed portion of the first hydrolyzate from the first hydrolysis vessel, wherein the percent amount of the water soluble monomeric sugars in the hydrolyzed portion is greater than 30% of the total amount of sugars in the hydrolyzed portion, and converting at least a portion of the water soluble monomeric sugars to a product mixture comprising the bio-product.

It is also disclosed that the percent amount of the remnant water soluble hemicellulose in the recirculated portion may be greater than a value selected from the group consisting of 30%, 50%, and 60% of the total amount of sugars in the recirculated portion.

It is further disclosed that the process may further comprise subjecting at least a portion of the remnant water soluble hemicellulose in the at least one pre-hydrolysis vessel to a second hydrolysis step, while pre-hydrolyzing a further portion of the water insoluble hemicellulose.

It is also disclosed that the process may further comprise subjecting the hydrolyzed portion removed from the first hydrolysis vessel to an refining hydrolysis step in a second hydrolysis vessel, to produce a second hydrolyzate, wherein the percent amount of the water soluble monomeric sugars in the second hydrolyzate is greater than 80% of the total amount of sugars in the second hydrolyzate.

It is further disclosed that at least one liquid composition selected from the group consisting of the liquid pre-hydrolysate and the first hydrolysate may be subjected to one or more separation steps obtaining at least a hemicellulose enriched fraction, and a monomers enriched fraction, wherein the concentration of water soluble hemicellulose in the hemicellulose enriched fraction is greater than the concentration of water soluble hemicellulose in the liquid composition, and wherein the concentration of water soluble monomeric sugars in the monomers enriched fraction is greater than the concentration of water soluble monomeric sugars in the liquid composition.

It is also disclosed that the hemicellulose enriched fraction may be at least the major part of the recirculated portion of the first hydrolyzate to at least one pre-hydrolysis vessel.

It is also disclosed that at least a portion of the monomers enriched fraction may be sent to the second hydrolysis vessel.

It is further disclosed that the first hydrolysis step b) may be conducted in the presence of mineral acid or acids. It is also disclosed that the pre-hydrolysis step a) may be conducted in the presence of mineral acid or acids recirculated from the first hydrolysis vessel.

It is further disclosed that the first hydrolysis step b) may be conducted at a pH which is at least 1 pH unit less than the pH in the pre-hydrolysis step a).

It is also disclosed that the pre-hydrolysis step a) and first hydrolysis step b) may be conducted at about the same temperature.

It is further disclosed that the pre-hydrolysis step a) may be conducted in both a continuous mode or a batch mode, but preferably in a batch mode.

It is also disclosed that the first hydrolysis step b) may be conducted in a continuous or semi-continuous mode.

It is further disclosed that the pre-hydrolysis step a) may comprise hydrothermally treating the water insoluble ligno-cellulosic feedstock in the presence of a fluid comprising water in liquid or steam phase, or a combination thereof, at a pre-hydrolysis temperature in a range from 130° C. to 200° C. and for a pre-hydrolysis time from 5 minutes to 180 minutes.

It is also disclosed that the first hydrolysis step b) may be conducted at a hydrolysis temperature in a range from 130° C. to 200° C.

It is further disclosed that the refining hydrolysis step may be conducted at a hydrolysis temperature in a range from 130° C. to 200° C. and for a hydrolysis time from 5 minutes to 180 minutes.

It is also disclosed that the bio-product may comprise at least a compound selected from the group consisting of ethylene glycol, propylene glycol, and a mixture thereof.

It is further disclosed that the conversion of the water soluble monomeric sugars to the bio-product may comprise the steps of:

a. Hydrogenating the water soluble monomeric sugars, by contacting at least a portion of the water soluble monomeric sugars with a hydrogenation catalyst in the presence of Hydrogen, at a hydrogenation pressure in the range of 30 bar to 150 bar and at a hydrogenation temperature in the range of 50° C. to 200° C., and for a hydrogenation time sufficient to produce a hydrogenated mixture comprising water and at least a sugar alcohol;

b. Conducting hydrogenolysis of at least a portion of the hydrogenated mixture, by contacting the at least a portion of the hydrogenated mixture with a hydrogenolysis catalyst in the presence of OH⁻ ions and Hydrogen, at a hydrogenolysis pressure in the range of 40 bar to 170 bar, at a hydrogenolysis temperature and for a hydrogenolysis time sufficient to produce a hydrogenolysis mixture comprising the bio-product, and c. Recovering the bio-product.

It is also disclosed that that the process may further comprise the steps of:
a. producing a hemicellulose-depleted ligno-cellulosic feedstock, and
b. converting the hemicellulose-depleted ligno-cellulosic feedstock to a cellulosic pulp.

DETAILED DESCRIPTION

Figure 1:
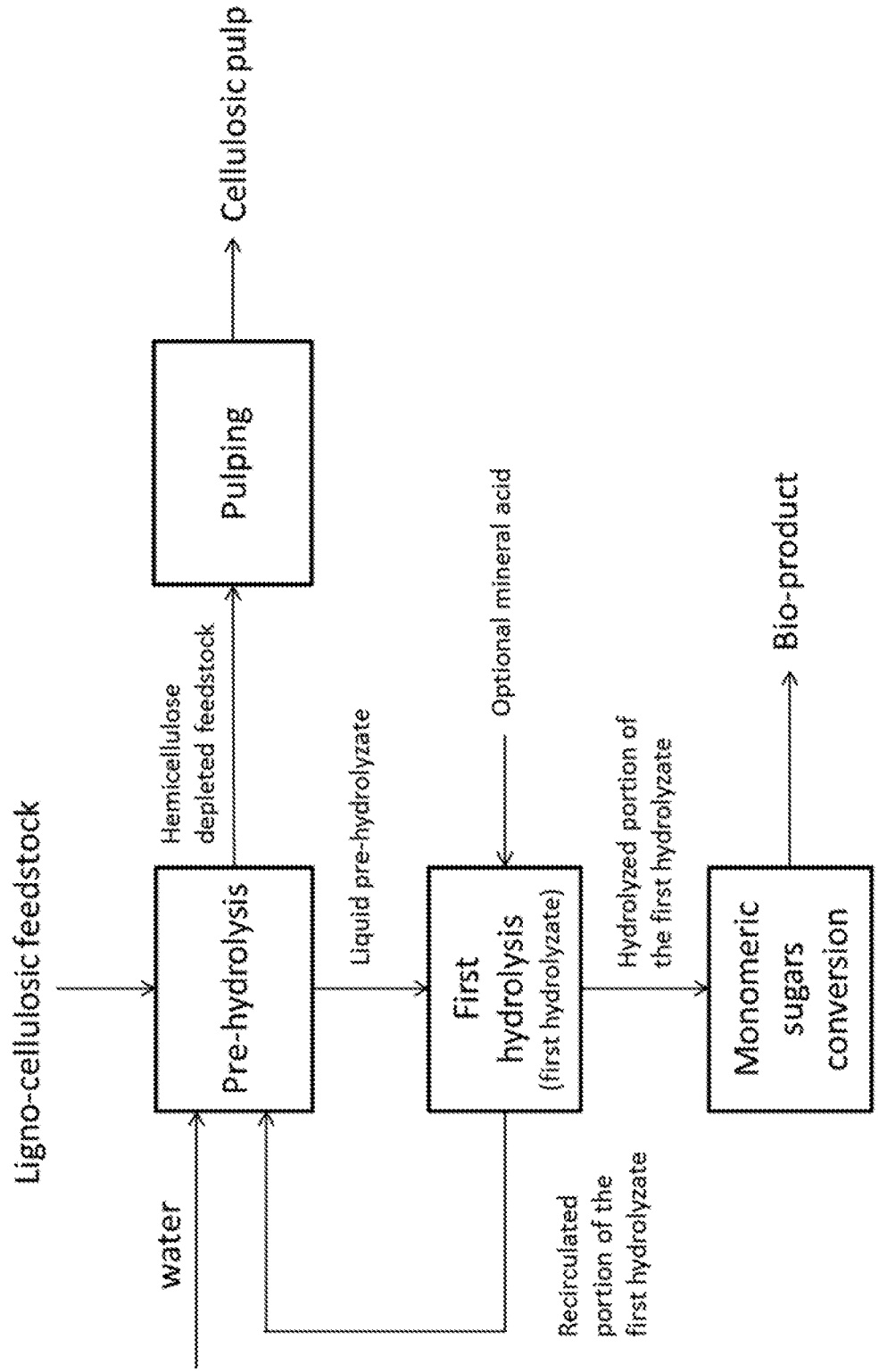
FIG. 1 is a schematic representation of the invention.

The disclosed process produces a bio-product from a ligno-cellulosic feedstock. A detailed description of a ligno-cellulosic feedstock may be found in WO2015028156A1, pp. 11-14. Preferably, the ligno-cellulosic feedstock is a softwood or a hardwood. The ligno-cellulosic feedstock comprises hemicellulose, cellulose and lignin, which are water insoluble, and the disclosed process produces the bio-product mainly from the hemicellulosic fraction of the feedstock.

By the terms "bio-product", or "bio-based product" it is meant a product derived from or synthesized by a renewable biological feedstock, such as, for example, an agricultural, forestry, plant, bacterial, or animal feedstock. A bio-based product differs from the corresponding petrochemical-derived product by the isotopic abundance of contained Carbon. It is known in art that there are three Carbon isotopes (namely $^{12}C$, $^{13}C$ and $^{14}C$), and that isotopic ratios of the isotopes of carbon, such as the $^{13}C/^{12}C$ carbon isotopic ratio or the $^{14}C/^{12}C$ carbon isotopic ratio, are different in petrochemical derived products and bio-based products due to different chemical processes and isotopic fractionation. In addition, radioactive decay of the unstable $^{14}C$ carbon radioisotope leads to different isotope ratios in bio-based products compared to petrochemical derived products. Measurements of isotopic abundance may be performed, for example, by liquid scintillation counting, accelerator mass spectrometry, or high precision isotope ratio mass spectrometry. Bio-based content of a product may be verified by ASTM International Radioisotope Standard Method D6866. ASTM International Radioisotope Standard Method D6866 determines bio-based content of a material based on the amount of bio-based carbon in the material or product as a percent of the weight (mass) of the total organic carbon in the material or product. Bio-based products will have a carbon isotope ratio characteristic of a biologically derived composition.

As the bio-product is obtained by converting the water soluble monomeric sugars derived mainly by the hemicellulose of the ligno-cellulosic feedstock, it is an objective of the disclosed process to extract, or solubilize, the majority of the hemicellulose to produce one or more liquid compositions comprising water and water soluble monomeric sugars.

Therefore, the ligno-cellulosic feedstock is first subjected to a pre-hydrolysis step in one or more pre-hydrolysis vessels to solubilize at least a portion of the water insoluble hemicellulose, thereby producing a liquid pre-hydrolyzate comprising water soluble hemicellulose. For the scope of the present disclosure, by the term "water soluble hemicellulose" are indicated all the water soluble sugars different from monomeric sugars, which are derived from the water insoluble hemicellulose of the ligno-cellulosic feedstock. This concept may be also expressed by introducing the degree of polymerization, or DP, which is usually defined as the number of monomeric units in a macromolecule or polymer or oligomer molecule. Stated in other words, water soluble hemicellulose are all the water soluble sugars derived from the hemicellulose having a DP which is greater than 1. Water soluble hemicellulose is then hydrolyzed to water soluble monomeric sugars (DP=1) to be converted to the bio-product.

At this first pre-hydrolysis step, the liquid pre-hydrolyzate may further comprise some amount of water monomeric sugars, even if the total percent amount of water soluble monomeric sugars is typically less than 10% of the total amount of sugars in the liquid hydrolyzate at this stage. The liquid pre-hydrolyzate may further comprise soluble non-sugar compounds derived from the lignocellulosic feedstock, such as for instance acetyl groups and acetic acid, which contributes to lower the pH of the pre-hydrolysis step and following process steps. Even if a portion of the cellulose of the ligno-cellulosic feedstock may be also solubilized during pre-hydrolysis, the total water soluble sugars of the liquid pre-hydrolyzate are derived mainly from the hemicellulose of the ligno-cellulosic feedstock. The amount of cellulose solubilized may be determined for instance by measuring the amount of cellulose in the ligno-cellulosic feedstock before and after the pre-hydrolysis step. The water soluble hemicellulose may comprise C5 and C6 sugars. C5 sugars are pentose-based sugars, wherein pentose is a monosaccharide with five carbon atoms. Xylose is an example of monomeric pentose sugar. C6 sugars are hexose-based sugars, being the hexose a monosaccharide with six carbon atoms. Glucose is an example of monomeric hexose sugar. In a preferred embodiment, xylose-based water soluble sugars are at least 50% of the total weight of water soluble hemicellulose.

The liquid pre-hydrolyzate from the pre-hydrolysis vessel or vessels is then received in a first hydrolysis vessel, wherein it is maintained at first hydrolysis conditions to promote the hydrolysis of the water soluble hemicellulose to monomeric sugars. In a preferred embodiment, these first hydrolysis conditions comprise conducting the first hydrolysis in more acidic conditions with respect to the pre-hydrolysis step. Apart from acidifying agents generated from the ligno-cellulosic feedstock during the pre-hydrolysis step, this acidic conditions may be obtained by adding a mineral acid from an external source. The liquid pre-hydrolyzate is therefore subjected to a first hydrolysis step to produce a first hydrolyzate contained in the first hydrolysis vessel, the first hydrolyzate comprising therefore water, water soluble monomeric sugars and remnant water soluble hemicellulose. By the term "remnant water soluble hemicellulose" are hereby indicated the water soluble sugars derived from the hemicellulose having a degree of polymerization greater than 1, thereby all the sugars of the first hydrolyzate, derived from the hemicellulose, which have not been hydrolyzed to monomers. Thereby, remnant water soluble hemicellulose may comprise also not monomeric sugars which have been partially hydrolyzed to polymers with a low degree of polymerization.

The percent amount of water soluble hemicellulose in the first hydrolyzate contained in the first hydrolysis vessel may vary over time to a great extent, depending on the temporal sequence used for receiving the liquid pre-hydrolyzate from the pre-hydrolysis vessel or vessels, which may not occur simultaneously. For instance, there may be time intervals during which the hydrolysis extent of the water soluble hemicellulose in the first hydrolyzate is very low, typically when a great amount of liquid pre-hydrolyzate has just been received from one or more pre-hydrolysis vessels. Thereby, in certain instances, the percent content by weight of the water soluble hemicellulose in the first hydrolysis vessel may be greater than 80% of the amount of total sugars. Correspondingly, the percent content by weight of monomeric water soluble sugars in the first hydrolysis vessel may be less than 20% of the amount of total sugars. On the other hand, there may be time intervals during which the hydrolysis extent of the water soluble hemicellulose in the first hydrolyzate is very high, being the percent content by weight of the monomeric sugars greater than 80% of the amount of total sugars. While these compositional limits of the first hydrolyzate may occur during operations, the percent amount by weight of remnant water soluble hemicellulose in the first hydrolyzate contained in the first hydrolysis vessel is preferably maintained in the range of from 30% to 80%, more preferably from 50% to 80%, and most preferably from 50% to 70%.

The disclosed process is characterized by recirculating a first portion of the first hydrolyzate from the first hydrolysis vessel to one or more pre-hydrolysis vessels, the first portion being a recirculated portion of the first hydrolyzate comprising water and remnant water soluble hemicellulose, and by removing a second portion of the first hydrolyzate from the first hydrolysis vessel, said second portion being a hydrolyzed portion of the first hydrolyzate comprising water and water soluble monomeric sugar or sugars to be converted to the bio-product by means of downstream process step or steps.

The recirculated portion of the first hydrolyzate and the hydrolyzed portion preferably have a different content of monomeric sugars and water soluble remnant hemicellulose, being the recirculated portion preferably more rich in water soluble remnant hemicellulose than the hydrolyzed portion. In a preferred embodiment, this is obtained by removing the two portions of the first hydrolyzate from the first hydrolysis vessel at different times, corresponding to different hydrolysis extents of the first hydrolyzate. In another embodiment, a portion of the first hydrolyzate is separated in two fractions, the first fraction being water soluble hemicellulose-enriched and the second fraction being monomeric sugars enriched. The first fraction is then recirculated in one or more pre-hydrolysis vessels.

Therefore, the first hydrolysis vessel acts as hydrolysis router, which is used for a) collecting the liquid pre-hydrolysate from one or more vessels, b) conducting a partial hydrolysis step of the liquid pre-hydrolysate to produce a first hydrolyzate having a time variable content of water soluble hemicellulose and monomeric sugars, c1) routing to upstream pre-hydrolysis vessels a recirculated portion of the first hydrolyzate preferably having a high content of water soluble hemicellulose, and c2) routing to downstream conversion steps a hydrolyzed portion of the first hydrolyzate preferably having a high content of water soluble monomeric sugars.

In the pre-hydrolysis vessel, the recirculated portion of the first hydrolyzate will be subjected to a second hydrolysis step, wherein the hydrolysis of remnant water soluble hemicellulose is continued. As the second hydrolysis step preferably occurs in the presence of ligno-cellulosic feedstock, a further portion of hemicellulose is pre-hydrolyzed producing new water soluble hemicellulose, thereby in the second hydrolysis step a more concentrated pre-hydrolyzate is also obtained, at the same time being characterized by a relevant concentration of hydrolyzed monomeric sugars and water soluble hemicellulose. As the first hydrolysis step is conducted in the presence of acidifying agents, which comprise organic acids generated from the ligno-cellulosic feedstock and optional added mineral acid, the portion of the first hydrolyzate recirculated in the pre-hydrolysis vessel comprises a portion of these acidifying agents, further promoting the hemicellulose solubilization. Thereby, the second hydrolysis step is also a second pre-hydrolysis step.

The pre-hydrolyzate obtained in this second hydrolysis step is then preferably reintroduced into the first hydrolysis vessel for hydrolyzing the remnant and the newly extracted water soluble hemicellulose.

The hydrolyzed portion of the first hydrolyzate which is removed from the first hydrolysis vessel may still comprise some water soluble hemicellulose, which cannot be converted directly to the bio-product; therefore, in a preferred embodiment, the hydrolyzed portion is further hydrolyzed in a separate vessel, which is a second hydrolysis vessel, wherein at least a portion of the water soluble hemicellulose is converted to monomeric sugars Taking into consideration that in the first hydrolysis vessel the extent of hydrolysis of the first hydrolyzate will vary over time, the composition of the hydrolyzed portion removed from the first hydrolysis vessel may be subjected to significant fluctuations; the refining hydrolysis step in the second hydrolysis vessel, in addition to increase the hydrolysis yield, is introduced to equalize the content of the water soluble monomeric sugars, thereby producing a second hydrolyzate having a more time-stable content of monomeric sugars with respect to the first hydrolyzate.

Therefore, according to one aspect of the invention, it is disclosed a multi-step hydrolysis process of water soluble hemicellulose, the hydrolysis steps being conducted in separated vessels, wherein at least one hydrolysis step is conducted in a pre-hydrolysis vessel or vessels.

Some of the advantages offered by the disclosed process are made evident by the following theoretical example. The example contains indicative parameters based on general knowledge and it is introduced to better explain the working principle.

Pre-hydrolysis conditions to solubilize 60% of the hemicellulose from a ligno-cellulosic feedstock (*Eucalyptus*): 160° C., 60 minutes. Pre-hydrolysis reactor operated in continuous mode.

Volume of the liquid pre-hydrolyzate: volume of the solid ligno-cellulosic feedstock=6:1. Exemplary total hydrolysis conditions: 160° C., pH=3. To reach 90% of hydrolysis of water soluble hemicellulose, the hydrolysis time is about 180 minutes.

Thereby, in the case that hydrolysis is performed as a single step process in a unique vessel, the hydrolysis vessel volume is preferably 3 times the volume of the pre-hydrolysis vessel.

In the case of disclosed process, reusing the pre-hydrolysis vessel to hydrolyze the recirculated portion of the first hydrolyzate in one subsequent pre-hydrolysis step of 60 minutes, the volume of the first hydrolysis vessel is reduced correspondingly by about one third. By varying the residence times of the liquid hydrolyzate and pre-hydrolyzate, the volume of the hydrolysis reactor according to the desired process strategy may be further optimized.

According to another aspect of the invention, it is disclosed a process to obtain an hydrolyzate comprising water soluble monomeric sugars, the process being distributed in more vessels, each having a specialized function: a pre-hydrolysis vessel, to produce a concentrated liquid pre-hydrolyzate, while conducting hydrolysis of previously extracted water soluble hemicellulose; a first hydrolysis vessel, for conducting a partial hydrolysis of the liquid pre-hydrolyzates received from the pre-hydrolysis vessel or vessels, and routing different portions of the first hydrolyzate according to process timing; and an optional second hydrolysis reactor, for performing a finishing hydrolysis step.

In FIG. 1 it is schematically represented a basic embodiment of the disclosed process. The ligno-cellulosic feedstock is inserted in a pre-hydrolysis vessel and subjected to a pre-hydrolysis step to solubilize at least a portion of the hemicellulose of the ligno-cellulosic feedstock. The pre-hydrolysis step is a hydrothermal treatment which occurs in the presence of a fluid comprising water. Water may be present in steam phase or liquid phase, or a mixture thereof, depending on pressure and temperature conditions in the pre-hydrolysis vessel. Therefore, water is added to the pre-hydrolysis vessel from an external source to the process and/or as a recycled liquid stream from the process. External water may be added as a pressurized liquid stream comprising water and/or as a steam stream. When a pressurized liquid stream comprising water is used, it is preferably inserted into the pre-hydrolysis vessel at a temperature which is about the pre-hydrolysis temperature. In the present specification, by the expression "about the same temperature" it is meant that the temperature difference is less than 20° C., preferably less than 10° C. In one embodiment, a pressurized liquid water stream and a steam stream are both added to the pre-hydrolysis vessel, simultaneously or sequentially, preferably from two separated inlets. An example of recycled liquid stream comprising water added to the pre-hydrolysis vessel is the recirculated portion of the first hydrolyzate of the disclosed process, but other recycled water streams may also be used. The recycled liquid stream or streams are preferably inserted into the pre-hydrolysis vessel at a temperature which is about the pre-hydrolysis temperature. As the external water represents the net water consumption of the pre-hydrolysis step, which should be minimized, the amount of external water added to the pre-hydrolysis vessel is preferably less than 50% of the amount of total water added to the pre-hydrolysis vessel. Thereby, according to one aspect of the invention, the disclosed process reduces the consumption of external water needed to conduct the process. Preferably, the amount of total water used in the pre-hydrolysis step is less than 8l/Kg of lignocellulosic feedstock on a dry basis.

Pre-hydrolysis temperature may be in the range from 130° C. to 200° C., preferably in the range from 140° C. to 180° C., more preferably in the range from 150° C. to 170° C. The pre-hydrolysis time may be in the range from 5 minutes to 180 minutes, preferably in the range from 10 minutes to 80 minutes, more preferably in the range from 20 minutes to 60 minutes. Pre-hydrolysis time may vary depending on the specific kind of ligno-cellulosic feedstock, pre-hydrolysis temperature and the quality of pulp to be produced.

The liquid pre-hydrolyzate, or a portion thereof, is introduced from the pre-hydrolysis vessel in the first hydrolysis vessel, which is operatively connected to the pre-hydrolysis vessel. By the expression "operatively connected" it is meant that two or more vessels are connected either directly or indirectly through an intermediate zone or apparatus. In the first hydrolysis vessel, the liquid pre-hydrolyzate is subjected to a first hydrolysis step by maintaining the first hydrolysis at conditions promoting the hydrolysis of the water soluble hemicellulose to monomeric sugars. The introduction of the liquid pre-hydrolyzate in the first hydrolysis vessel may proceed discontinuously, thereby the percent amount of water soluble monomeric sugars and water soluble hemicellulose may vary over time in a broad range, as the hydrolysis of water soluble hemicellulose proceeds. The first hydrolysis step may be conducted at a hydrolysis temperature in a range from 130° C. to 200° C., preferably in the range from 140° C. to 180° C., more preferably in the range from 150° C. to 170° C. Preferably, the first pre-hydrolysis step and the first hydrolysis step are conducted at about the same temperature, being possible in this case to heat the pre-hydrolysis vessel and the first hydrolysis vessel by a unique heat source, which is preferably steam pressurized at a unique pressure. To promote hydrolysis in the first hydrolysis vessel, the first hydrolysis step is preferably conducted at more acidic conditions than the pre-hydrolysis step. Apart from natural acidifying agents generated during the pre-hydrolysis step, such as acetic acid and other organic acids, which may give rise to a liquid pre-hydrolyzate having a pH in the range of 3 to 5.5, in a preferred embodiment the first hydrolysis occurs in the presence of a mineral acid or acids, such as sulfuric acid, hydrochloric acid, and nitric acid, which may be added to the first hydrolysis vessel or to the liquid pre-hydrolyzate before or while entering the first hydrolysis vessel. The mineral acid is preferably added in an amount and at a concentration sufficient to conduct the first hydrolysis step at a pH which is at least 0.5 pH unit, preferably at least 1 pH unit, more preferably 2 pH units less than the pH in the pre-hydrolysis step.

Two portion of the first hydrolyzate are then removed from the first hydrolysis vessel. A first portion of the first hydrolyzate comprising water and remnant water soluble hemicellulose is recirculated to the pre-hydrolysis vessel for further hydrolysis of the remnant water soluble hemicellulose. Preferably, the percent amount of the remnant water soluble hemicellulose in the recirculated portion is greater than 30% of the total amount of sugars in the recirculated portion, more preferably greater than 50%, even more preferably greater than 60%. Thereby, the recirculated portion of the first hydrolyzate is preferably removed from the first hydrolysis vessel when the hydrolysis extent of the first is low. In the case that the first hydrolysis step and the pre-hydrolysis step are conducted at about the same temperature, the partially hydrolyzed mixture may be reintroduced directly into the pre-hydrolysis vessel. In the case that the first hydrolysis step is conducted at a hydrolysis temperature different from the pre-hydrolysis temperature, which is typically greater than the pre-hydrolysis temperature, the recirculated portion of the first hydrolyzate may be stored in a storage tank provided of suitable heating/cooling means to set the temperature of the recirculated portion to the proper temperature, which is preferably about the pre-hydrolysis temperature, before being introduced in the pre-hydrolysis vessel.

The recirculated portion of the first hydrolyzate further comprises some natural acidifying agents present in the first hydrolysis vessel, and eventually also a portion of optional mineral acid or acids added to the first hydrolysis vessel. In this case, the concentration of the mineral acid in the pre-hydrolysis vessel is less than the concentration in the first hydrolysis vessel, due to the dilution effect of the external water added to the pre-hydrolysis vessel.

In the pre-hydrolysis vessel, at least a portion of the remnant water soluble hemicellulose reintroduced undergoes a second hydrolysis step. The second hydrolysis step is preferably conducted at pre-hydrolysis temperature and time conditions in the presence of lignocellulosic feedstock, thereby a further portion of water insoluble hemicellulose is pre-hydrolyzed to water soluble hemicellulose, being the second hydrolysis and pre-hydrolysis further promoted by the organic acidifying agents and optional mineral acid contained in the recycled portion of the first hydrolyzate. In a preferred embodiment, the ligno-cellulosic feedstock present in the pre-hydrolysis vessel in the second hydrolysis step is a fresh ligno-cellulosic feedstock and the process increases the concentration of total soluble sugars in the liquid pre-hydrolyzate and the first hydrolyzate. In another embodiment, at least a portion of the lignocellulosic feedstock present in the pre-hydrolysis vessel during the second hydrolysis has been subjected to a previous pre-hydrolysis step, thereby being a hemicellulose partially depleted lignocellulosic feedstock. This further pre-hydrolysis step is in this case promoted by the recycled acids. Thereby, the disclosed process improves also the total pre-hydrolysis yield which is the percent amount of the hemicellulose originally contained in the ligno-cellulosic feedstock solubilized in the process.

From the pre-hydrolysis vessel, a second portion of the first hydrolyzate comprising water and water soluble monomeric sugars is also removed. This second portion is a hydrolyzed portion of the first hydrolyzate and it has a percent amount of water soluble monomeric sugars greater than 30% of the total amount of sugars in the hydrolyzed portion, preferably greater than 50%, more preferably greater than 70%. Thereby, the hydrolyzed portion of the first hydrolyzate is preferably removed from the first hydrolysis vessel when the hydrolysis extent of the first is high, being in this case the removal discontinuous.

The pre-hydrolysis step may be conducted in continuous or batch mode, depending on the way to operate the lignocellulosic feedstock and/or the hemicellulose-depleted lignocellulosic feedstock. The hemicellulose-depleted ligno-cellulosic feedstock is the ligno-cellulosic feedstock produced after the pre-hydrolysis step or steps. Thereby, the hemicellulose-depleted lignocellulosic feedstock comprises mainly cellulose and lignin, and optionally a portion of the hemicellulose which has not been removed by the pre-hydrolysis step or steps.

In order for the pre-hydrolysis to be continuous, it is not necessary that the ligno-cellulosic feedstock is continuously introduced into the pre-hydrolysis vessel, but it can be introduced at steady aliquots or pulses. Thus there are moments when there is no ligno-cellulosic feedstock entering the pre-hydrolysis vessel. But, over time, the total mass introduced into the pre-hydrolysis vessel equals the total mass removed from the pre-hydrolysis vessel. One distinguishing feature between a continuous and a batch pre-hydrolysis step is that, in a continuous process, the pre-hydrolysis is occurring or progressing at the same time that either the ligno-cellulosic feedstock is introduced into the pre-hydrolysis vessel and/or the hemicellulose depleted ligno-cellulosic feedstock is removed from the pre-hydrolysis vessel. Another way to state this is that the pre-hydrolysis step in the pre-hydrolysis vessel occurs while simultaneously, or at the same time, removing the hemicellulose depleted ligno-cellulosic feedstock from the pre-hydrolysis vessel. Such removal is done in a continuous manner which includes an aliquot or pulse removal. In continuous mode, the hemicellulose-depleted ligno-cellulosic feedstock is preferably removed from the pre-hydrolysis vessel in a slurry form with the liquid pre-hydrolyzate. The slurried ligno-cellulosic feedstock is then separated at least in the liquid pre-hydrolyzate and the solid hemicellulose-depleted ligno-cellulosic feedstock. Separation may be obtained by means of at least a technique selected from the group consisting of draining of liquid hydrolyzate by gravity, centrifugation, and pressing. A washing step of the hemicellulose-depleted ligno-cellulosic feedstock may also be introduced to improve removal of the soluble sugars from the solids.

In the case that pre-hydrolysis is conducted in batch mode, the solid hemicellulose-depleted ligno-cellulosic feedstock is removed from the pre-hydrolysis vessel after the pre-hydrolysis step has been completed. In one embodiment, the hemicellulose-depleted ligno-cellulosic feedstock after pre-hydrolysis is subjected to subsequent treatment steps in the pre-hydrolysis vessel before being removed. These treatment steps may include treating the hemicellulose-depleted ligno-cellulosic feedstock with a chemical liquor to produce a cellulosic pulp, as typically occurs in pulping processes.

It is noted that, in a batch pre-hydrolysis, liquids may be introduced and/or removed while pre-hydrolysis is occurring or progressing. Namely, the liquid pre-hydrolyzate may be removed from the pre-hydrolysis vessel while the pre-hydrolysis is occurring or progressing. Removal may occurs continuously or discontinuously. In the same way, the recirculated portion of the hydrolyzate may be introduced continuously or discontinuously in the pre-hydrolysis vessel while the pre-hydrolysis is occurring or progressing.

The first hydrolysis step is preferably conducted in a continuous mode. In order for the first hydrolysis to be continuous, it is not necessary that the liquid pre-hydrolyzate is continuously introduced into the first hydrolysis vessel, but it can be introduced at steady aliquots or pulses. Thus there are moments when there is no liquid pre-hydrolyzate entering the pre-hydrolysis vessel. But, over time, the total mass introduced into the first hydrolysis vessel equals the total mass removed from the first hydrolysis vessel. One distinguishing feature between a continuous and a batch first hydrolysis step is that, in a continuous process, the first hydrolysis step is occurring or progressing at the same time that either the liquid pre-hydrolyzate is introduced into the first hydrolysis vessel and/or the recirculated portion and/or the hydrolyzed portion of the first hydrolyzate are removed from the first hydrolysis vessel. Another way to state this is that the first hydrolysis step in the first hydrolysis vessel occurs while simultaneously, or at the same time, removing the recirculated portion and/or the hydrolyzed portion of the first hydrolyzate from the first hydrolysis vessel. Such removal is done in a continuous manner which includes an aliquot or pulse removal.

The water soluble monomeric sugars are then converted to the bio-product. The bio-product may be selected from the groups of polyols, diols, alcohols, and carboxylic acids. The conversion may comprise biological conversion steps, such as a fermentative step by a microbial organism, or thermochemical steps, or both. In one embodiment, the bio-product comprises lactic acid, which is produced by bacterial fermentation.

In a preferred embodiment, the bio-product comprises a compound selected from the group consisting of ethylene glycol, propylene glycol, or a mixture thereof. In this case, the bio-product is preferably produced by means of a catalytical conversion process. Prior to catalytical conversion, the hydrolyzate is preferably subjected to one or more conditioning steps to remove impurities from the hydrolyzate.

The hydrolyzate may be subjected to a removal step of suspended solids before feeding the disclosed process, as suspended solids may obstruct downstream equipments. Removal of suspended solids may include for instance, but is not limited to, the use of a press, a decanter, a centrifuge, a filter, a flocculating agent, a micro-filter, a plate and frame filter, a crossflow filter, a pressure filter, a vacuum filter, or a combination thereof.

The hydrolyzate may further comprises compounds which are not monomeric sugars, such as dissolved cations and anions derived from the ligno-cellulosic feedstock, acetic acid, furfural, as well as water soluble hemicellulose and oligomeric sugars which have not been hydrolyzed to monomers. Thereby the hydrolyzate may be subjected to one or more refining steps in order to greatly reduce these impurities. The refining steps may comprise chromatographic separation by means of ion-exchange agents and size-exclusion agents.

In an embodiment, the hydrolyzate is subjected to one or more concentration steps, which may be carried out using any technique known to those of skill in the art. For example, concentration may be carried out by subjecting the liquid biomass feedstream to membrane filtration, evaporation, or a combination thereof. Without being limiting, microfiltration (with a pore size of 0.05 to 5 microns) may be carried out to remove particles, followed by ultrafiltration (500-2000 kDalton raw cut off) to remove soluble lignin and other large molecules and reverse osmosis to increase the concentration of soluble compounds, followed by evaporation.

Preferably, the hydrolyzate entering the catalytical conversion process has a dry matter content by weight which is greater than 3%, more preferably greater than 5% even more preferably greater than 10%, even yet more preferably greater than 15%, and most preferably greater than 20%.

The catalytic conversion process is preferably conducted according to the teaching of WO2015028156, which is herein incorporated by reference. Briefly, The catalytic conversion process comprises a hydrogenation step of the water soluble monomeric sugars to produce a hydrogenated mixture comprising water and a mixture of sugar alcohols, and a hydrogenolysis step of the hydrogenated mixture, to produce the a hydrogenolysis mixture comprising the bio-product. The bio-product is then recovered preferably by means of at least one distillation step of the hydrogenolysis mixture.

In the disclosed process, the hemicellulose-depleted lignocellulosic feedstock may be used to produce valuable products derived preferably from the cellulose fraction and optionally from the lignin fraction, and in this case it may be subjected to further treatment steps. In a preferred embodiment, the disclosed process to produce the bio-product from the monomeric sugars is integrated in a pulp making process, and hemicellulose-depleted ligno-cellulosic feedstock is converted to a cellulosic pulp, and the integration may occur as a retrofit of an already existing plant. The conversion of the hemicellulose-depleted ligno-cellulosic feedstock to the cellulosic pulp may be conducted by means of well-known pulp processes, such as kraft pulping, soda pulping, and sulfite pulping. The conversion may be conducted at least in part in the pre-hydrolysis vessel, following the pre-hydrolysis step or steps. In this case, after pre-hydrolysis step or steps the hemicellulose-depleted ligno-cellulosic feedstock is maintained in the pre-hydrolysis vessel and treated by means of a chemical liquor.

In another embodiment the hemicellulose-depleted ligno-cellulosic feedstock is used to produce a hydrolyzed mixture comprising monomeric sugars derived from the cellulosic fraction, which are then converted to a second bio-product, for example to a biofuel, such as ethanol, or another biochemical. Therefore, the hemicellulose-depleted ligno-cellulosic feedstock may be subjected to a further hydrothermal treatment, optionally in the presence of catalysts, such as mineral acids, followed by a biological conversion step or steps, which may comprise one or more enzymatic hydrolysis steps and a fermentative step. The further hydrothermal treatment is preferably conducted in a vessel different from the pre-hydrolysis vessel.

Figure 2:
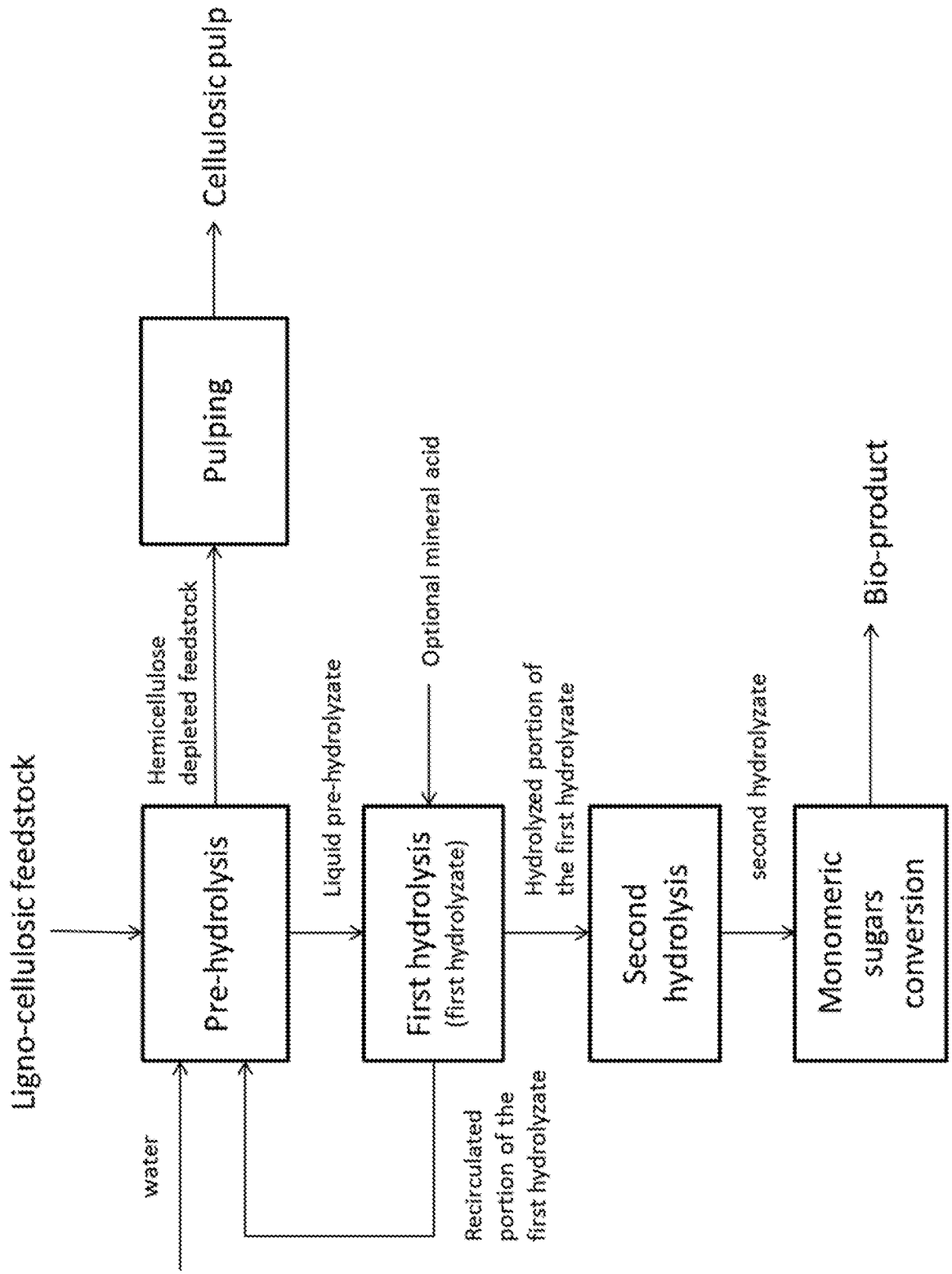
FIG. 2 is a schematic representation of another embodiment of the invention.

The hydrolyzed portion of the first hydrolyzate may further comprise some water soluble hemicellulose, which in a preferred embodiment depicted in FIG. 2 is introduced in a second hydrolysis vessel, which is operatively connected to the first hydrolysis vessel, and subjected to an refining hydrolysis step. The scope of the optional second hydrolysis step is to produce a second hydrolyzate characterized by a percent amount of the water soluble monomeric sugars greater than 80% of the total amount of sugars in the second hydrolyzate, preferably greater than 90%, most preferably greater than 95%.

The second hydrolysis temperature may be in the range from 130° C. to 200° C., preferably in the range from 140° C. to 180° C., more preferably in the range from 150° C. to 170° C. The second hydrolysis time may be in the range from 5 minutes to 180 minutes, preferably in the range from 5 minutes to 90 minutes, more preferably in the range from 5 minutes to 60 minutes. Optionally, some mineral acid may be added also to the second hydrolysis vessel. In a preferred embodiment, the pre-hydrolysis, the first hydrolysis and the second hydrolysis are conducted at about the same temperature. As the hydrolyzed portion of the first hydrolyzate may be introduced in the second hydrolysis reactor discontinuously or it may have a time-variable hydrolysis extent, the second hydrolysis time may be tuned during operations in order to equalize the produced second hydrolyzate, preferably avoiding overexposure of the monomeric sugars to harsh hydrolysis conditions which could degrade the monomeric sugars to degradation products such as furfural, 5-hydroxymethyl furfural, formic acid, and levulinic acid.

The second hydrolysis step is preferably conducted in continuous mode.

Figure 3:
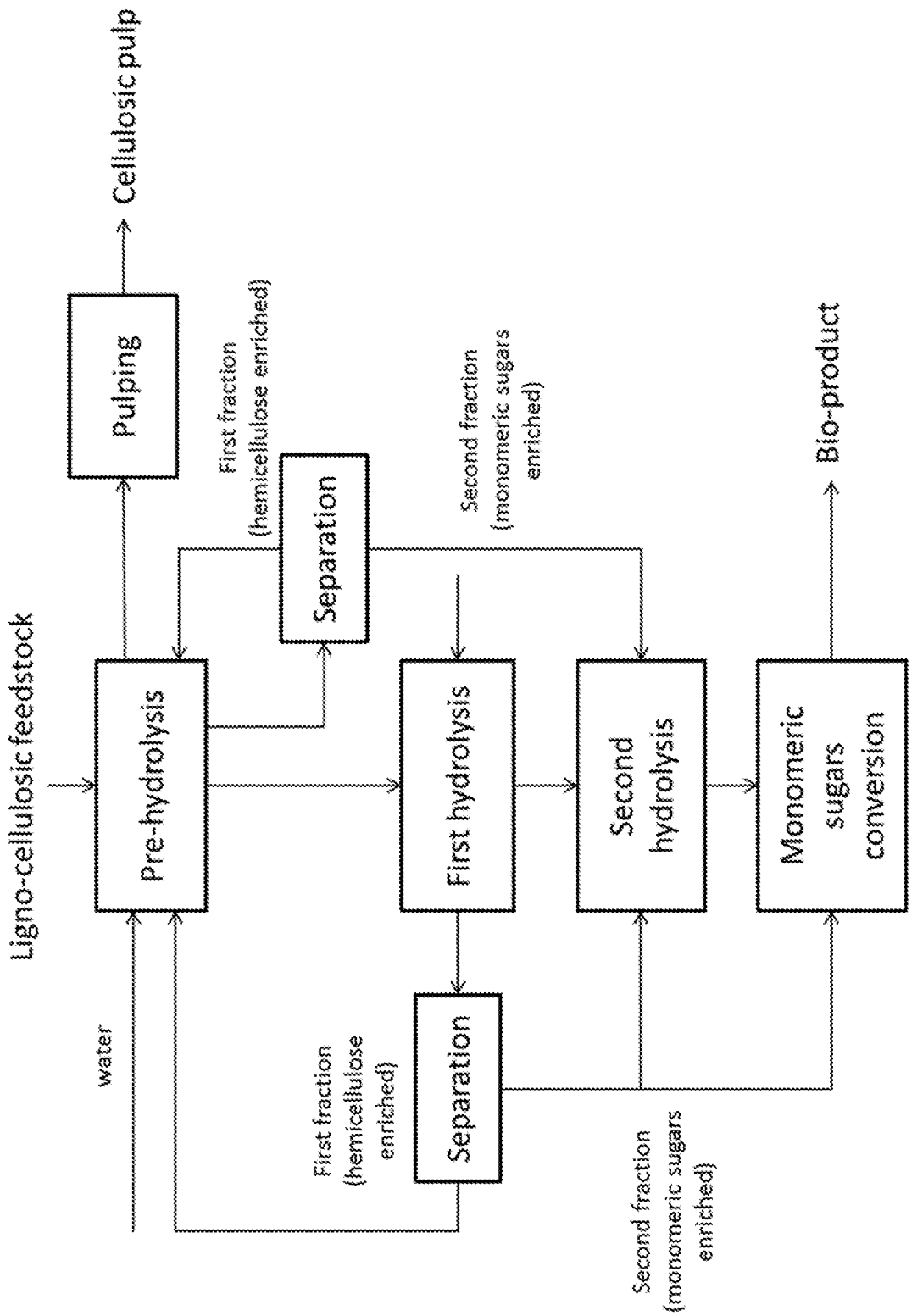
FIG. 3 is a schematic representation of a further embodiment of the invention.

As one of the scopes of the disclosed process is to distribute the hydrolysis of the water soluble hemicellulose to monomeric sugars in more than one vessel, it may be convenient to selectively recirculate water soluble hemicellulose in the pre-hydrolysis vessel, while advancing the water soluble monomeric sugars to post-hydrolysis steps of the disclosed process to prevent sugar degradation. Thereby, in an embodiment, depicted in FIG. 3, it is introduced a selective separation of the first hydrolyzate and/or the liquid pre-hydrolyzate, the selective separation comprising one or more separation steps, to produce at least a first liquid fraction enriched of water soluble hemicellulose with respect to the liquid composition entering the separation step or steps, i.e the first hydrolyzate and/or the liquid pre-hydrolyzate. Thereby, the first liquid fraction, which is a hemicellulose enriched fraction, is characterized by having a concentration of water soluble hemicellulose which is greater than the concentration of water soluble hemicellulose in the liquid composition. The hemicellulose enriched fraction may then be then added to the pre-hydrolysis vessel for being further hydrolyzed. The hemicellulose enriched fraction may be the majority of the recirculated portion of the first hydrolyzate, thereby being more than 50% by volume of the recirculated portion of the first hydrolyzate, more preferably more than 60%, even more preferably more than 70%, and most preferably more than 80% of the recirculated portion of the first hydrolyzate. The separation further produces a second liquid fraction enriched of water soluble monomeric sugars which may be sent directly to the conversion steps of monomers to the bio-product, thereby bypassing any further hydrolysis step. Thereby, the second liquid fraction, which is a monomers enriched fraction, is characterized by having a concentration of water soluble monomeric sugars which is greater than the concentration of water soluble monomeric sugars in the liquid composition entering the separation step or steps. As a complete separation of water soluble hemicellulose and water soluble monomeric sugars may be hard to be obtained, the monomers enriched fraction may further comprise some water soluble hemicellulose, which may be sent to the optional second hydrolysis vessel for refining hydrolysis step. On the other hand, the hemicellulose enriched fraction may further comprise some monomeric sugars, which are recirculated in the pre-hydrolysis vessel. Separation of the first hydrolyzate and/or the liquid pre-hydrolyzate preferably occurs outside the respective vessels. In another embodiment, the separation means are integrated into the corresponding vessel and only the first liquid fraction is removed from the vessel. Separation may be for instance performed by means of a crossflow filter, as disclosed in WO2010114468, or any other cross filter technique. The cross flow filter as disclosed in WO2010114468 use a tubular ceramic filter body with a filter coating with pore size in the range 0.2 to 1.9 micrometer adapted for green liquor filtering, and for oligomer filtering the pore size is adapted such that liquid and monomers may pass the filter coating as a permeate and but not oligomers kept in the retentate flow circulating through the tubular ceramic filter body.

Figure 4:
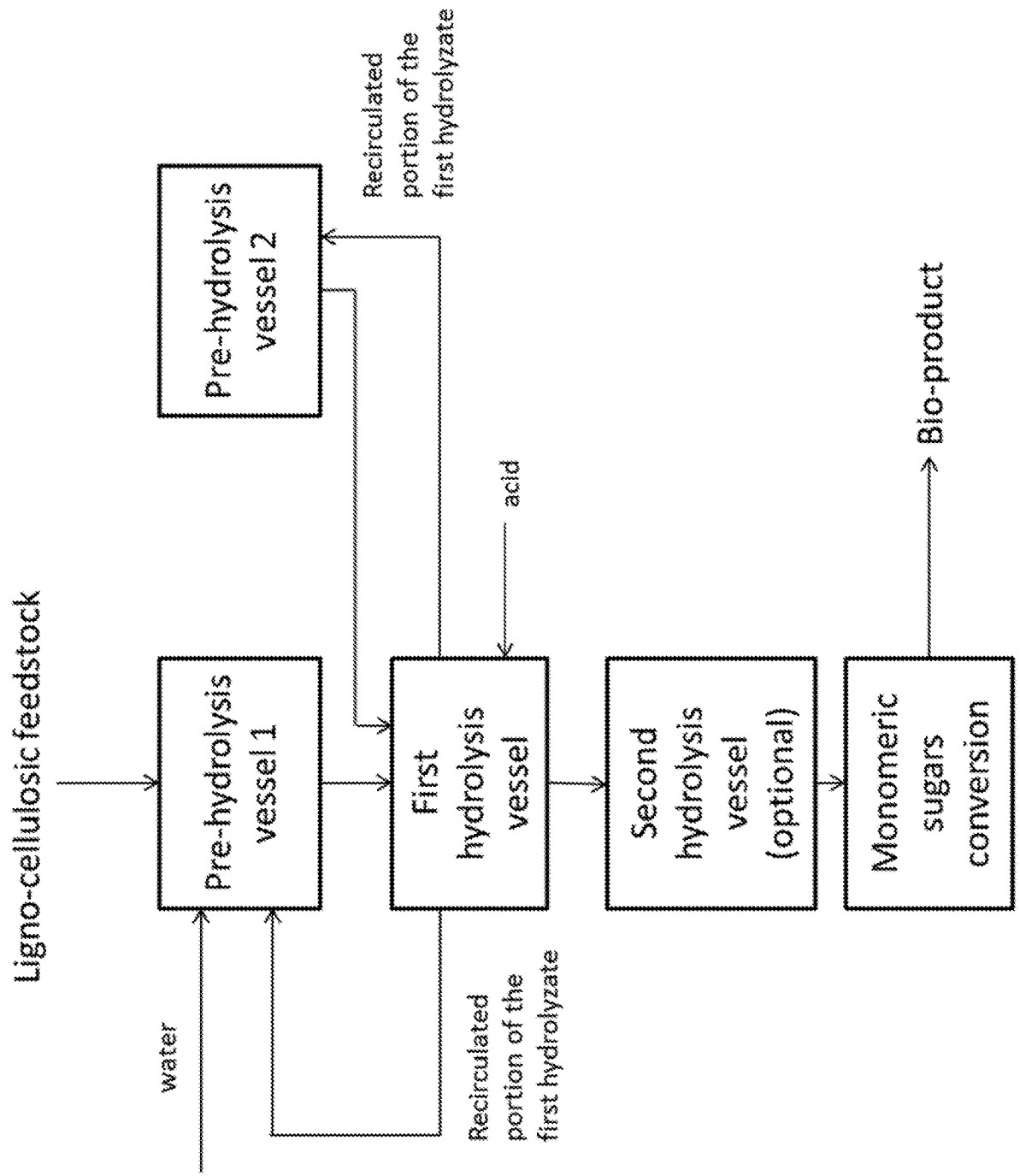
FIG. 4 is a schematic representation of a fourth embodiment of the invention.

In a preferred embodiment, the ligno-cellulosic feedstock may be pre-hydrolyzed in more than one pre-hydrolysis vessels, which are operatively connected to the first hydrolysis vessel. In FIG. 4, it is depicted the exemplary embodiment of two pre-hydrolysis vessels operatively connected to the first hydrolysis vessel. The first hydrolysis vessel acts as a common hydrolysis vessel, receiving the liquid sugar mixtures produced in the pre-hydrolysis vessels. The recirculated portion of the first hydrolyzate may then be introduced in one or both the pre-hydrolysis vessels. The liquid pre-hydrolyzates produced in different pre-hydrolysis vessels are preferably introduced into the first hydrolysis vessel sequentially, or not simultaneously, in order to maintain the filling level of the first hydrolysis vessel in a specific target range, which may be varied according to different operating procedure.

In one embodiment, the pre-hydrolysis vessels are operated in a batch mode, and the process comprises the steps of feedstock loading, feedstock heating, pre-hydrolysis, pre-hydrolyzate removal, and feedstock discharging, each having a proper step time. Pre-hydrolysis and pre-hydrolyzate removal may occur simultaneously. Recirculation of the first hydrolyzate in the pre-hydrolysis vessels may occur during feedstock heating and/or during pre-hydrolysis. In a preferred embodiment, the hemicellulose-depleted feedstock is further subjected to a chemical treatment in the pre-hydrolysis vessels before being discharged from the pre-hydrolysis vessels, as typically occurs in pulping process. Thereby, additional steps related to chemical pulping may also be included. Each batch process will therefore have a total cycle time, and the pre-hydrolysis time is a fraction of the total cycle time. Total cycle time may be from 150 to 450 minutes, preferably from 200 to 400 minutes, and most preferably from 240 to 350 minutes. The batch pre-hydrolysis vessels may be operated with a reciprocal cycle time delay, thereby, at a certain time, different steps are conducted in the pre-hydrolysis vessels. For instance, the liquid pre-hydrolyzate is preferably discharged from the first pre-hydrolysis vessel to the hydrolysis vessel when a portion of the first hydrolyzate has been recirculated or while is being recirculated in the second pre-hydrolysis vessel. Preferably the process cycles of the batch pre-hydrolysis vessels are synchronized in such a way that the liquid pre-hydrolyzates from all the pre-hydrolysis vessels are not present or discharged at the same time in the first hydrolysis vessel. Alternatively, the process cycles of the batch pre-hydrolysis vessels are preferably synchronized in such a way that at least a pre-hydrolysis vessel contains a recirculated portion of the first hydrolyzate. In an embodiment, the hydrolyzed portion of the first hydrolyzate is discontinuously removed from the first hydrolysis vessel; in this case, in order to advance the hydrolysis extent of the first hydrolysis step, the batch pre-hydrolysis vessels and the first hydrolysis vessel are operated in such a way that no liquid pre-hydrolyzate enters the first hydrolysis vessel for at least 5 minutes, preferably at least 10 minutes, more preferably at least 30 minutes before the hydrolyzed portion of the first hydrolyzate is removed from the first hydrolysis vessel.

The invention claimed is:

1. A process for producing a bio-product from a water insoluble ligno-cellulosic feedstock comprising cellulose, hemicellulose and lignin, the process comprising the steps of:
   a. pre-hydrolyzing a portion of the water insoluble hemicellulose in one or more pre-hydrolysis vessels, to produce a liquid pre-hydrolyzate comprising water and water soluble hemicellulose;
   b. receiving the liquid pre-hydrolyzate in a first hydrolysis vessel from at least one pre-hydrolysis vessel;
   c. subjecting the liquid pre-hydrolyzate to a first hydrolysis step to produce a first hydrolyzate comprising water, water soluble monomeric sugars and remnant water soluble hemicellulose;
   d. recirculating a portion of the first hydrolyzate to the at least one pre-hydrolysis vessel, wherein the portion of the first hydrolyzate comprises water-soluble monomeric sugars and remnant water soluble hemicellulose,
   e. removing a portion of the first hydrolyzate from the first hydrolysis vessel, wherein a percent amount of the water soluble monomeric sugars in the hydrolyzed portion is greater than 30% of a total amount of sugars in the hydrolyzed portion, and
   f. converting at least a portion of the water soluble monomeric sugars to a product mixture comprising the bio-product.

2. The process of claim 1, wherein a percent amount of the remnant water soluble hemicellulose in the recirculated portion of the first hydrolyzate is greater than a value selected from the group consisting of 30%, 50%, or 60% of a total amount of sugars in the recirculated portion.

3. The process of claim 1, further comprising subjecting at least a portion of the water soluble hemicellulose in the at least one pre-hydrolysis vessel to a second hydrolysis step, while pre-hydrolyzing a further portion of the water insoluble hemicellulose.

4. The process of claim 1, further comprising subjecting the hydrolyzed portion of the first hydrolyzate removed from the first hydrolysis vessel to a refining hydrolysis step in a second hydrolysis vessel to produce a second hydrolyzate, wherein a percent amount of the water soluble monomeric sugars in the second hydrolyzate is greater than 80% of a total amount of sugars in the second hydrolyzate.

5. The process of claim 1, wherein at least one liquid composition selected from the group consisting of the liquid pre-hydrolyzate or the first hydrolyzate is subjected to one or more separation steps obtaining at least a hemicellulose enriched fraction and a monomers enriched fraction, wherein a concentration of water soluble hemicellulose in the hemicellulose enriched fraction is greater than a concentration of water soluble hemicellulose in the liquid composition, and wherein a concentration of water soluble monomeric sugars in the monomers enriched fraction is greater than a concentration of water soluble monomeric sugars in the liquid composition.

6. The process of claim 5, wherein the hemicellulose enriched fraction is at least a major part of the recirculated portion of the first hydrolyzate to the at least one pre-hydrolysis vessel.

7. The process of claim 6, wherein at least a portion of the monomers enriched fraction is sent to a second hydrolysis vessel.

8. The process of claim 1, wherein the first hydrolysis step b) is conducted at a pH which is at least 0.5 pH unit less than the pH in the pre-hydrolysis step a).

9. The process of claim 8, wherein the first hydrolysis step b) is conducted in a presence of mineral acid or acids.

10. The process of claim 9, wherein the pre-hydrolysis step a) is conducted in a presence of mineral acid or acids recirculated from the first hydrolysis vessel.

11. The process of claim 1, wherein the pre-hydrolysis step a) and first hydrolysis step b) are conducted at about a same temperature.

12. The process of claim 1, wherein the pre-hydrolysis step a) is conducted in a batch mode.

13. The process of claim 12, wherein the first hydrolysis step b) is conducted in a continuous or semi-continuous mode.

14. The process of claim 1, wherein the pre-hydrolysis step a) comprises hydrothermally treating the water insoluble ligno-cellulosic feedstock in a presence of a fluid comprising water in liquid or steam phase, or a combination thereof, at a pre-hydrolysis temperature in a range from 130° C. to 200° C. and for a pre-hydrolysis time from 5 minutes to 180 minutes.

15. The process of claim 14, wherein the first hydrolysis step b) is conducted at a hydrolysis temperature in a range from 130° C. to 200° C.

16. The process of claim 15, wherein a refining hydrolysis step is conducted at a hydrolysis temperature in a range from 130° C. to 200° C. and for a hydrolysis time from 5 minutes to 180 minutes.

17. The process of claim 1, wherein the bio-product comprises at least a compound selected from the group consisting of ethylene glycol, propylene glycol, or a mixture thereof.

18. The process of claim 17, wherein the conversion of the water soluble monomeric sugars to the bio-product comprises the steps of:
hydrogenating the water soluble monomeric sugars by contacting at least a portion of the water soluble monomeric sugars with a hydrogenation catalyst in the presence of hydrogen at a hydrogenation pressure in a range of 30 bar to 150 bar and at a hydrogenation temperature in a range of 50° C. to 200° C., and for a hydrogenation time sufficient to produce a hydrogenated mixture comprising water and at least a sugar alcohol;
conducting hydrogenolysis of at least a portion of the hydrogenated mixture by contacting the portion of the hydrogenated mixture with a hydrogenolysis catalyst in a presence of $OH^-$ ions and hydrogen at a hydrogenolysis pressure in a range of 40 bar to 170 bar at a hydrogenolysis temperature and for a hydrogenolysis time sufficient to produce a hydrogenolysis mixture comprising the bio-product, and
recovering the bio-product.

19. The process of claim 1, further comprising the steps of:
producing a hemicellulose-depleted ligno-cellulosic feedstock, and
converting the hemicellulose-depleted ligno-cellulosic feedstock to a cellulosic pulp.

20. The process of claim 1, wherein the bio-product comprises a polyol.

21. The process of claim 1, wherein the bio-product comprises a diol.

22. The process of claim 1, wherein the bio-product comprises an alcohol.

23. The process of claim 1, wherein the bio-product comprises a carboxylic acid.

24. The process of claim 1, wherein the bio-product comprises a lactic acid.

25. The process of claim 1, wherein the bio-product comprises an ethylene glycol.

26. The process of claim 1, wherein the bio-product comprises a propylene glycol.

27. The process of claim 1, wherein the bio-product comprises a mixture of two or more chemicals selected from polyol, diol, alcohol, carboxylic acid, lactic acid, ethylene glycol, or propylene glycol.

* * * * *